United States Patent [19]
Aitken et al.

[11] 3,963,578

[45] June 15, 1976

[54] STABILIZATION OF PHOSPHOENOL PYRUVATE CARBOXYLASE

[75] Inventors: Walter Brent Aitken; Ronald Wayne Bussian, both of Newark; Robert Carroll Menson; Venkatachalam Narayanswamy, both of Wilmington, all of Del.

[73] Assignee: E. I. Du Pont de Nemours and Company, Wilmington, Del.

[22] Filed: Dec. 20, 1974

[21] Appl. No.: 535,139

[52] U.S. Cl. .................... 195/63; 195/99; 195/103.5 R; 424/2
[51] Int. Cl.$^2$ .................. C07G 7/02; G01N 31/14
[58] Field of Search ........... 195/63, 68, 99, 103.5 R; 424/2

[56] References Cited
UNITED STATES PATENTS

| | | | |
|---|---|---|---|
| 3,296,094 | 1/1967 | Cayle | 195/63 |
| 3,539,450 | 11/1970 | Deutsch | 195/68 |
| 3,717,550 | 2/1973 | Ziffer | 195/63 |

*Primary Examiner*—David M. Naff

[57] ABSTRACT

Phosphoenol pyruvate carboxylase is stabilized to have a shelf life of six months or more by incorporating the phosphoenal pyruvate carboxylase in an aqueous solution containing from 0.002 to 0.05 molar sodium phosphate, from 1 to 10, and preferably 3 to 8, m molar aspartate, from 0.02 to 0.1 m molar ethylene diamine tetraacetic acid, from 0.6 to 3.15, and preferably 0.8 to 1.2, molar ammonium sulfate and up to 20 volume percent glycerol. The sodium phosphate acts as a buffer to maintain the pH of the solution at from 6.0 to 6.8.

6 Claims, No Drawings

STABILIZATION OF PHOSPHOENOL PYRUVATE CARBOXYLASE

BACKGROUND OF THE INVENTION

The present invention relates to a composition containing phosphoenol pyruvate carboxylase having improved shelf life. Phosphoenol pyruvate carboxylase finds use in automatic analyzers for determining the amount of carbon dioxide in blood. The human body generates a large amount of carbon dioxide; only a small portion of which is reutilized, for instance, in urea formation. The rest must be eliminated. One way in which carbon dioxide is eliminated is through the blood stream, and the concentration of carbon dioxide in the blood stream has a profound effect on body function. A moderate elevation in the concentration of carbon dioxide in the blood supply to the brain, for example, greatly enhances cerebral circulation. Abnormal concentrations of carbon dioxide in the blood stream, then, are either the product of or in some circumstances, the cause of a variety of illnesses. For this reason, the measurement of carbon dioxide content in the blood stream or other body fluids is an important measurement in medical diagnostics.

Only a small portion of the carbon dioxide introduced into the bloodstream remains in the physically dissolved state. The rest is converted into carbonic acid by the catalytic action of carbonic anhydrase. The carbonic acid in turn dissociates into hydrogen ions and bicarbonate ions at the pH of blood. The determination of the amount of bicarbonate ions present by a spectrophotometric instrument can be achieved by coupling of the bicarbonate ions to a material(s) which exhibit(s) light absorption. The amount of this material present is determined photometrically and the amount of bicarbonate originally present is thus determined. Phosphoenol pyruvate carboxylase is used for this purpose. The reaction involved is:

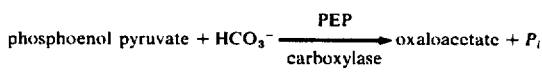

where PEP carboxylase stands for phosphoenol pyruvate carboxylase and $P_i$ stands for inorganic phosphorus. The thus-formed oxaloacetate is further reacted:

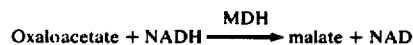

where MDH stands for malate dehydrogenase, and NADH and NAD, respectively, stand for the reduced and oxidized form of nicotinamide adenine dinucleotide. The instruments can be set up either to measure the rate of conversion of NADH to NAD or the end point of the reaction. When using the rate process, the process comprising mixing measured amounts of the body fluid to be tested with an excess amount of the substrate and a measured amount of enzyme, phosphenol pyruvate/phosphoenol pyruvate carboxylase, an excess of an activator such as fructose 1,6 diphosphate, an excess amount of malate dehydrogenase, and the reduced form of nicotinamide adenine dinucleotide; and determining the change in concentration of the reduced form of nicotinamide adenine dinucleotide in the mixture so formed while maintaining the system at a substantially constant pH. If desired carbonic anhydrase can be added to the mixture. Carbonic anhydrase acts to convert $CO_2$ into carbonic acid which turns into bicarbonate under the condition used. The reduced form of nicotinamide adenine dinucleotide absorbs light very strongly between about 290 and about 380 millimicrons while the oxidized form does not. Thus, the rate of disappearance of the reduced form is directly proportional to the decrease in absorbance of light and can be measured readily using a conventional spectrophotometric procedure. Since the rate of oxidation of the reduced form of nicotinamide adenine dinucleotide is also proportional to the rate of formation of oxaloacetate and the rate of formation of oxaloacetate is a function of the concentration of bicarbonate in the system, the rate of decrease in light absorbance at from 290 to about 380 millimicrons can be used as a direct measure of the original concentration of bicarbonate in the sample fluid. This determination can be made rapidly and accurately in automated equipment. One of the problems involved in performing these determinations is that the phosphoenol pyruvate carboxylase tends to lose its activity on storage thereby causing erroneous rate determinations. The rate process uses substantially less of the expensive enzyme than the end point process and for this reason is preferred so long as comparable accuracy is obtained.

DESCRIPTION OF THE INVENTION

The present invention is directed to a stable enzyme composition containing phosphoenol pyruvate carboxylase. It is known that phosphoenol pyruvate carboxylase can be isolated from any of *Escherichia coli*, all strains including strain B and strain W, *Salmonella typhinurium*, Brevibacterium flavin, which are essentially identical for this purpose, *Bacillus stearothermophillus*, *Arthrobacter globiformis*, which are similar for this purpose, as well as other bacteria such as *Acetobacter xylinum*. Undoubtedly other bacteria can be used for this purpose. The composition exhibits a loss in activity of 1.5% or less per month at V max for at least 6 months. As used herein, loss in enzyme activity is determined by comparing its activity with that of the fresh sample in a test pack used in an automatic clinical analyzer which measures the rate of conversion of NADH to NAD.

Generally the composition contains from 0.002 to 0.05 molar sodium phosphate which serves to buffer the solution at from pH 6.0 to pH 6.8. Lower concentrations of sodium phosphate may not provide sufficient buffer capacity but otherwise could be used. Higher concentrations of up to 0.2 molar can be used but are not preferred. The 0.2 molar figure approximates the limit of solubility of sodium phosphate at 4°C. which is the normal storage temperature for the product. The 0.05 M figure is the preferred upper limit because it provides enough buffering capacity to smooth the fluctuations in stability which have been observed and yet is low enough in ionic strength not to contribute significantly to the overall ionic strength in the final composition. This is important because the enzyme, phosphoenol pyruvate carboxylase, is inhibited by ionic strength in the final composition.

Generally the composition contains 1 to 10 m molar aspartate with from 3 to 8 m molar aspartate being the preferred range. The aspartate improves the stability of the composition. Although higher concentrations probably will work as well, their use increases the cost without additional benefit since the preferred range is sufficient to saturate the aspartate binding site.

Generally the composition will contain from 0.02 to 0.1 m molar ethylene diamine tetraacetic acid (EDTA), which is added for its prophylactic effect in case of contamination of the composition with heavy metal ions. Phosphoenol pyruvate carboxylase is known to be a sulfhydryl labile enzyme and this lability is accentuated by the presence of heavy metal ions.

Ammonium sulfate provides increased protection of the enzyme. For the level of stability achieved herein the lower limit is about 0.6 molar with about 0.8 to 1.2 molar being preferred. It is undesirable to use significantly more ammonium sulfate than is necessary to achieve the desired stability because of the ionic strength inhibition of the enzyme in the final product. Thus, the preferred upper limit of ammonium sulfate is about 1.2 molar, although up to about 3.75 molar which is the saturation point at 4°C. can be used.

It is preferred to include some glycerol in the composition. Generally if glycerol is used the amount used will be from 3 to 20 volume percent of the overall composition. Although glycerol alone in the absence of ammonium sulfate definitely provides added protection to the enzyme, in the presence of ammonium sulfate only minor benefit in stability is gained. It is used herein to provide other benefits which result in increased precision of the value as produced by the final product.

Generally the composition will contain from 1 to 4,000, and preferably 1 to 100, International Units per ml of phosphoenol pyruvate carboxylase. Below about 1 International Unit per ml there is insufficient enzyme present to be practical for most uses. One hundred International Units is about the highest concentration of enzyme that can be achieved by an impure preparation technique such as is disclosed herein. When using a pure preparation technique, a concentration of about 4,000 International Units per ml can be obtained.

DESCRIPTION OF THE PREFERRED EMBODIMENTS

Escherichia coli cells (454 grams commercial grade strain B), which have been grown in a Kornberg glucose salt medium, are suspended (38% w/v) in a buffer solution, at a pH of 7.8, composed of 0.01 M $Na_3PO_4$, 0.005 M aspartic acid, and 0.0001 M EDTA. The cells are disrupted in a homogenizer, and the cell debris is removed by centrifugation.

The supernatant liquid, about 1955 ml, is pooled and 391 ml of a 10% aqueous solution of streptomycin sulfate is added. The resulting precipitate is removed by centrifugation and the supernatant is made 0.6 saturated with $(NH_4)_2SO_4$ by addition of 835 g of $(NH_4)_2SO_4$. The resulting precipitate is collected by centrifugation and then dissolved in the buffer solution described above to a volume of 303 ml. A 60 ml portion is diluted with 120 ml of the above buffer. Seventy-seven ml of saturated ammonium sulfate solution are added. The resulting precipitate is removed by centrifugation. To the supernatant solution is added 98 ml of saturated ammonium sulfate solution. The resulting precipitate was collected by centrifugation and dissolved in the above buffer to a total volume of 34 ml. This is dialyzed against 3400 ml of a solution of the composition indicated in the examples in Table I. The composition is stored in 0.05 to 0.075 ml aliquots which contain from 12 to 14 International Units per ml of the enzyme phosphoenol pyruvate carboxylase in an inert transparent plastic pack at 4°C. for the time indicated in the particular example and then tested for enzyme activity which is reported as the percent lost as compared with the enzyme activity tested on the fresh composition. Examples 11-13 were stored in small glass vials rather than plastic packs. In addition to the materials reported in Table I, several of the examples contained additioned materials. The composition of Examples 8 and 9 contained 0.5 molar $MgCl_2$. The composition of Examples 8, 9, and 10 contained 7 mg per ml, bovine serum albumin. Example 10 also contained 1 m molar dithioerythritol. In Examples 11, 12, and 13 the solution was prepared to the final composition in a low concentration of sodium phosphate and sufficient $Na_2HPO_4$ added to buffer the composition to the pH reported in Table I. The composition of Examples 11-13 also contained 0.1 M $MgSO_4$. Examples 11-13 illustrate that too low an amount of aspartate results in a rapid loss of enzyme activity. In Example 15 the composition contained 0.5 mg per ml of bovine serum albumin and 5 m molar dithioerythritol. Examples 15 and 16 illustrate that glycerol has a stabilizing effect on the composition in the absence of ammonium sulfate. In Example 17 the solution was prepared to the final composition in a low concentration of sodium phosphate and sufficient $NaH_2PO_4$ added to buffer the composition to the pH reported in Table I. In Examples 18, 19, and 20 the solution was prepared to the final composition in a low concentration of sodium phosphate and sufficient $Na_3PO_4$ added to buffer the composition to the pH reported in Table I. Examples 19 and 20 show the rapid loss in activity of the enzyme when stored at pH 7.8. In Table I $NaPO_4$ stands for sodium phosphate, Asp stands for aspartate, EDTA stands for ethylene diamine tetraacetic acid, and Gly stands for glycerol.

TABLE I

| Example | $NaPO_4$ M | pH | Asp mM | $NH_4SO_4$ M | EDTA mM | Gly vol. % | Stability Day | % Loss |
|---|---|---|---|---|---|---|---|---|
| 1 | 0.05 | 6.4 | 5.0 | 1.0 | 0.1 | 10 | 168 | 8.5 |
| 2 | 0.05 | 6.4 | 5.0 | 1.0 | 0.1 | 10 | 170 | 8.9 |
| 3 | 0.05 | 6.4 | 5.0 | 1.0 | 0.1 | 10 | 117 | 4.3 |
| 4 | 0.05 | 6.4 | 5.0 | 1.0 | 0.1 | 10 | 42 | 2.0 |
| 5 | 0.01 | 6.4 | 5.0 | 1.0 | 0.1 | 5.0 | 141 | 7.9 |
| 6 | 0.01 | 6.55 | 5.0 | 1.0 | 0.1 | 10 | 98 | 5.8 |
| 7 | 0.01 | 6.53 | 5.0 | 1.0 | 0.1 | 10 | 168 | 5.4 |
| 8 | 0.025 | 6.4 | 3.75 | 1.0 | 0.025 | 10 | 168 | 7.9 |
| 9 | 0.025 | 6.4 | 3.75 | 1.0 | 0.025 | 10 | 150 | 5.1 |
| 10 | 0.023 | 6.4 | 3.45 | 1.0 | 0.023 | 10 | 168 | 8.1 |
| 11 | | 7.73 | 1.35 | 1.0 | 0.1 | 36.5 | 11 | 6.0 |
| 12 | | 7.73 | 2.70 | 1.0 | 0.1 | 36.5 | 13 | 6.0 |
| 13 | | 7.73 | 8.19 | 1.0 | 0.1 | 36.5 | 11 | 1.0 |
| 14 | 0.01 | 6.4 | 5.0 | 0.4 | 0.1 | 10 | 141 | 13.1 |
| 15 | 0.01 | 7.8 | 5.0 | | 0.05 | | 30 | 13.0 |
| 16 | 0.01 | 7.8 | 5.0 | | 0.05 | 12.5 | 30 | 6.0 |

TABLE I-continued

| Example | NaPO₄ M | pH | Asp mM | NH₄SO₄ M | EDTA mM | Gly vol. % | Stability Day | % Loss |
|---|---|---|---|---|---|---|---|---|
| 17 | | 6.0 | 5.0 | 1.0 | 0.1 | 10 | 174 | 8.9 |
| 18 | | 6.8 | 5.0 | 1.0 | 0.1 | 10 | 174 | 8.9 |
| 19 | | 7.8 | 5.0 | 1.0 | 0.1 | 10 | 140 | *22.1 |
| 20 | | 7.8 | 5.0 | 1.0 | 0.1 | 36.5 | 184 | *65.4 |

We claim:

1. A stable aqueous enzyme composition wherein the enzyme is phosphoenol pyruvate carboxylase and the stabilizer comprises from about 1 to about 10 m molar aspartate, from about 0.02 to about 0.1 m molar ethylene diamine tetraacetic acid, from about 0.6 to about 3.75 molar ammonium sulfate, and sufficient sodium phosphate to maintain the pH of the composition at from 6.0 to 6.8.

2. The composition of claim 1 wherein the amount of ammonium sulfate present is from 0.8 to 1.2 molar.

3. The composition of claim 2 wherein from 0.002 to 0.05 molar sodium phosphate is present.

4. The composition of claim 3 wherein from 3 to 20 volume percent glycerol is present.

5. The composition of claim 4 wherein from 3 to 8 m molar aspartate is present.

6. The composition of claim 5 wherein the enzyme is isolated from *Escherichia coli*.

* * * * *